US011160499B2

(12) United States Patent
Bonomi et al.

(10) Patent No.: US 11,160,499 B2
(45) Date of Patent: Nov. 2, 2021

(54) DEVICE, SYSTEM AND METHOD FOR ESTIMATING THE ENERGY EXPENDITURE OF A PERSON

(71) Applicant: KONINKLIJKE PHILIPS N.V., Eindhoven (NL)

(72) Inventors: Alberto Giovanni Bonomi, Eindhoven (NL); Francesco Sartor, Eindhoven (NL); Gabriele Papini, Eindhoven (NL); Erik Gosuinus Petrus Schuijers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 31 days.

(21) Appl. No.: 15/571,051

(22) PCT Filed: Dec. 19, 2016

(86) PCT No.: PCT/EP2016/081631
§ 371 (c)(1),
(2) Date: Nov. 1, 2017

(87) PCT Pub. No.: WO2017/108640
PCT Pub. Date: Jun. 29, 2017

(65) Prior Publication Data
US 2018/0249951 A1    Sep. 6, 2018

(30) Foreign Application Priority Data

Dec. 22, 2015   (EP) ..................................... 15202091

(51) Int. Cl.
*A61B 5/00*    (2006.01)
*A61B 5/024*   (2006.01)
*A61B 5/11*    (2006.01)

(52) U.S. Cl.
CPC ........ *A61B 5/4866* (2013.01); *A61B 5/02438* (2013.01); *A61B 5/1118* (2013.01); *A61B 5/6802* (2013.01); *A61B 5/681* (2013.01)

(58) Field of Classification Search
CPC . A61B 5/4866; A61B 5/6802; A61B 5/02438; A61B 5/1118; A61B 5/681; A61B 5/222; A61B 5/02
See application file for complete search history.

(56) References Cited

U.S. PATENT DOCUMENTS 4,312,358 A  *  1/1982  Barney ............... A61B 5/02438
                                                 235/91 H
4,586,515 A  *  5/1986  Berger ................. A61B 5/1121
                                                     600/595
(Continued)

FOREIGN PATENT DOCUMENTS

CN          103083002 A   *   5/2013
CN          103284705 A       9/2013
(Continued)

OTHER PUBLICATIONS

Achten et al., Heart Rate Monitoring Applications and Limitations, Sports Med, 2003, vol. 33(7), pp. 517-538 (Year: 2003).*
(Continued)

*Primary Examiner* — Jacqueline Cheng
*Assistant Examiner* — Tho Q Tran

(57) ABSTRACT

The present invention relates to a device for accurately estimating the energy expenditure of a person, in particular by which the effect of cardiovascular drift is taken into account. The device comprises an input unit (10) for obtaining a movement signal (13) representing physical activity of the person and a heart rate signal (15) representing the heart rate of the person, a cardiovascular drift determination unit (16) for determining cardiovascular drift phases (17) from said movement signal (13) and either said heart rate signal
(Continued)

(15) and/or one or more cardiovascular drift related signals (23) carrying information on one or more of amount of sweat, weight loss, temperature rise, blood lactate concentration and physical fatigue of the person, a correction unit (18) for correcting the heart rate signal (15) generated and representing the heart rate during a cardiovascular drift phase, and an estimation unit (20) for estimating the energy expenditure of the person from the corrected heart rate signal (19).

50 Claims, 7 Drawing Sheets

(56) References Cited

U.S. PATENT DOCUMENTS

| | | | | |
|---|---|---|---|---|
| 5,012,820 | A * | 5/1991 | Meyer | A61B 5/224 600/595 |
| 7,507,203 | B2 * | 3/2009 | Sebastian | A61B 5/0062 600/300 |
| 2002/0055694 | A1 * | 5/2002 | Halperin | A61B 5/11 601/41 |
| 2008/0107303 | A1 * | 5/2008 | Kim | G06F 3/0304 382/103 |
| 2010/0130873 | A1 * | 5/2010 | Yuen | A61B 5/165 600/484 |
| 2010/0160798 | A1 * | 6/2010 | Banet | A61B 5/02125 600/490 |
| 2011/0257542 | A1 | 10/2011 | Russell | |
| 2012/0083705 | A1 | 4/2012 | Yuen et al. | |
| 2015/0327804 | A1 * | 11/2015 | Lefever | A61B 5/0205 600/483 |
| 2017/0258407 | A1 * | 9/2017 | Shirai | A61B 5/7275 |

FOREIGN PATENT DOCUMENTS

| | | | |
|---|---|---|---|
| CN | 103610457 A | * | 3/2014 |
| WO | WO2013038296 A1 | | 3/2013 |
| WO | WO2015058923 A1 | | 4/2015 |

OTHER PUBLICATIONS

Pettitt et al., A theoretical method of using heart rate to estimate energy expenditure during exercise, International Journal of Sports Science & Coaching, Sep. 2007, pp. 319-327 (Year: 2007).*
Yu, Z. et al., "Comparison of heart rate monitoring with indirect calorimetry for energy expenditure evaluation", Journal of Sport and Health Science, vol. 1, No. 3, 2012.
Haskell, W. et al., "Simultaneous measurement of heart rate and body motion to quantitate physical activity", Med Sci Sports Exerc, vol. 25 No. 1, 1993.
PCT International Search Report, International Application No. PCT/EP2016/081631, dated Mar. 6, 2017.
Mattsson C. M., et al., "Reversed Drift in Heart Rate but Increased Oxygen Uptake at Fixed Work Rate During 24 h Ultra-Endurance Exercise", Scandinavian Journal of Medicine & Science in Sports,Apr. 1, 2010 (Apr. 1, 2010), p. 298, XP055346749.
Yang Y. et al., "An Exercise-Driven Heart Rate Statistical Process Model", Fusion, 2012 15th International Conference on Information Fusion, pp. 432-438.
Le et al., "A Dynamic Heart Rate Prediction Model for Training Optimization in Cycling", in Proceedings of 7th ISEA Conference 2008, pp. 1-6.
Bonomi AG et al., "Advances in Physical Activity Monitoring and Lifestyle Interventions in Obesity", International Journal of Obesity (2012) 36, 167-177.

* cited by examiner

DEVICE, SYSTEM AND METHOD FOR ESTIMATING THE ENERGY EXPENDITURE OF A PERSON

CROSS-REFERENCE TO RELATED APPLICATIONS

The present application claims the benefit under 35 U.S.C. § 371 of International Application No. PCT/EP2016/081631, filed on Dec. 19, 2016, which claims the benefit of European Patent Application No. EP15202091.3, filed on Dec. 22, 2015. These applications are hereby incorporated by reference herein in their entirety.

FIELD OF THE INVENTION

The present invention relates to a device, system and method for estimating the energy expenditure of a person.

BACKGROUND OF THE INVENTION

Physical activity can reduce the risk of developing certain diseases, such as obesity or hypertension and improve the overall well-being and quality of life of a person. An accurate and objective quantification of the physical activity is therefore becoming more and more essential, especially to support public health research and intervention programs and clarify the dose-response relation between physical activity and health. The use of accelerometers is very common to predict energy expenditure, as e.g. described in Bonomi AG, W. K. (2011), Advances in physical activity monitoring and lifestyle intervention in obesity, International Journal of Obesity, 1-11. They are cheap, simple to use and wearable. However, it is commonly admitted that some physical activities may be misinterpreted by such devices. As an example, it is difficult to accurately estimate energy expenditure during activities such as cycling, in particular for accelerometers worn on the wrist or at the waist. Indeed, very little motion is picked up by the accelerometer, resulting in a significant underestimation of the energy expenditure. Hence, adding a heart rate (HR) sensor leads to a more accurate estimation of the energy expenditure, especially when the HR-based prediction equation is personalized according to subject characteristics (such as age, gender, BMI, etc.) and/or individual fitness level (HR at rest, $VO_2max$, etc.). If the HR sensor is furthermore integrated in a wearable sensor (e.g. in a belt or in a wrist), the greater accuracy is achieved without negatively impacting the ease-of-use.

Over the past years, many studies have shown that physical activity can reduce the risk of developing several chronic diseases, such as obesity or hypertension and improve the overall well-being and quality of life. An accurate quantification of the physical activity is therefore becoming more and more essential, especially to support intervention programs. The use of accelerometers is very common to predict energy expenditure, but it is known that some physical activities (especially the ones that demand higher efforts) may be misinterpreted.

WO 2015/058923 A1 discloses a device for estimating the energy expenditure of a person with an increased accuracy. The device comprises a movement sensor for detecting physical activity of the person and for generating a movement signal, a heart rate sensor for detecting the heart rate of the person and for generating a heart rate signal, an estimation unit for estimating the energy expenditure of the person from said movement signal and/or said heart rate signal, and a control unit for controlling said estimation unit to switch between an non-activity mode in which only the movement signal is used for estimating the energy expenditure if no physical activity of the person has been detected and an activity mode in which the movement signal and/or the heart rate signal is used for estimating the energy expenditure if physical activity of the person has been detected.

SUMMARY OF THE INVENTION

It is an object of the present invention to provide a device, system and method for more accurately estimating the energy expenditure of a person with less complexity and reduced additional efforts and means.

In a first aspect of the present invention a device for estimating the energy expenditure of a person is presented comprising:

an input unit for obtaining a movement signal representing physical activity of the person and a heart rate signal representing the heart rate of the person, a cardiovascular drift determination unit for determining cardiovascular drift phases from said movement signal and either said heart rate signal and/or one or more cardiovascular drift related signals carrying information on one or more of amount of sweat, weight loss, temperature rise, blood lactate concentration and physical fatigue of the person, a correction unit for correcting the heart rate signal generated and representing the heart rate during a cardiovascular drift phase, and an estimation unit for estimating the energy expenditure of the person from the corrected heart rate signal.

In a further aspect of the present invention a system for estimating the energy expenditure of a person is presented comprising:

a movement sensor for detecting physical activity of the person and for generating a movement signal, a heart rate sensor for detecting the heart rate of the person and for generating a heart rate signal, and a device for estimating the energy expenditure of a person as disclosed herein.

In yet further aspects of the present invention, there are provided a corresponding method, a computer program which comprises program code means for causing a computer to perform the steps of the method disclosed herein when said computer program is carried out on a computer or processor as well as a non-transitory computer-readable recording medium that stores therein a computer program product, which, when executed by a computer or processor, causes the method disclosed herein to be performed.

Preferred embodiments of the invention are defined in the dependent claims. It shall be understood that the claimed system, method, computer program and medium have similar and/or identical preferred embodiments as the claimed device and as defined in the dependent claims.

Generally, when an individual/a person is physically active, energy expenditure and oxygen consumption are linearly related to heart rate. The present invention is based on the recognition that several physiological factors causing cardiovascular drift act modifying the relationship between HR and energy expenditure. Cardiovascular drift is defined as any increase in HR that is unrelated to any changes in oxygen consumption and energy expenditure. Factors influencing cardiovascular drift are for example: muscle fatigue (increase in central motor command), increase in core body temperature, heat exposure, vasodilatation, de-hydration, and hormonal influences such as catecholamine (adrenaline and noradrenalin). All of these factors are very common in daily life and may especially arise after exercise of moderate and vigorous intensity. Therefore, devices and method aimed at estimating energy expenditure from physiological data such as heart rate may suffer from the influence of cardiovascular drift.

Additionally, cardiovascular drift has a subject-specific and activity-dependent nature. HR drift is proportional to the intensity of the physical activity carried out, and it will begin after a certain elapsed time depending on the cardio-respiratory fitness level of such individual. For instance, if two individuals of same body weight or size, age and gender but different fitness level are asked to run at a given speed (e.g. 10 km/h), it can be observed that the unfit individual will show an HR drift much earlier and higher than the fit individual. For the same fitness level higher exercise intensity (20 km/h vs. 10 km/h speed) will elicit an earlier HR drift.

HR based estimates of energy expenditure are affected by cardiovascular drift. Cardiovascular drift causes overestimation errors of energy expenditure during physical activity as well as during the recovery phase following physical activity. Cardiovascular drift can for example originate during exercise due to muscle fatigue, dehydration and heat, which causes an abnormal elevation in HR without any corresponding increase in oxygen consumption and energy expenditure. In addition, after exercise HR can remain substantially high until the drift-causing factor has been recovered. This would mean that even after exercise, cardiovascular drift still alters HR and negatively impact interpretation algorithms based on physiological data. Energy expenditure may still be overestimated during the recovery phase after exercise because of elevated HR above the resting level. Moreover, algorithms aimed at determining physical effort, activity type, and stress level using HR data may suffer from either cardiovascular drift during activity and from elevated HR during activity recovery.

The present invention solves this overestimation by adding a HR drift correction to the original energy expenditure estimation. The HR drift correction is based on the physical activity of the person, such as e.g. physical activity type, physical activity intensity, physical activity elapsed time, physical activity history and fitness level. The HR drift is then used to correct the detected HR, e.g. subtracted from the detected (current) HR, and the corrected HR is then used to estimate energy expenditure so that no overestimation occurs. This correction of HR data for cardiovascular drift may be further used to improve the accuracy of any prediction algorithm aimed at interpreting HR to determine a user context or condition, such as activity type, stress level, physical effort or physical fitness.

In addition to physical activity said heart rate signal and/or one or more cardiovascular drift related signals carrying information on one or more of amount of sweat, weight loss, temperature rise, blood lactate concentration and physical fatigue of the person is used for determining the cardiovascular drift phases.

The device, system and method according to the present invention may not only explicitly detect the exact phase or state at which the heart rate measurement is, e.g. which moment of the cardiovascular drift (e.g. in active phase versus rest phase) is currently present. Generally, it is detected that a phase of cardiovascular drift is present, i.e. that currently there is cardiovascular drift. Furthermore, by means of modeling the exact phase may not explicitly be detected, but only a notion of the probability of being in a certain phase may be provided.

In an embodiment said cardiovascular drift determination unit is configured to determine the onset, duration, end and/or likelihood of cardiovascular drift phases. This information can then be advantageously used to further improve the correction of the HR signal. The onset may e.g. be used to simplify quantification of the cardiovascular drift. On the other hand, the likelihood may be easier to determine than e.g. the onset.

In another embodiment said cardiovascular drift determination unit is configured to determine cardiovascular drift phases during a physical activity phase and during a recovery phase succeeding a physical activity phase. Different ways for determination of the cardiovascular drift phases and for HR correction may be applied for a physical activity phase compared to a recovery phase. Determining the likelihood of cardiovascular drift phases may e.g. include that the current state and the previous state are considered. For instance, when the current state is resting state whereas the previous state was a physical activity state (e.g. a running state) for some time, the likelihood of drift is high.

Said cardiovascular drift determination unit may particularly be configured to determine, during a physical activity phase, a rising phase, a steady phase and a cardiovascular drift phase. Thus, the drift determination and the HR correction may be even further fine-tuned and improved. For instance, if properly modeled, the rising phase would be due to that it takes some time before the heart is pumping at a certain frequency, the steady phase would be due to the fact that no drift is present yet (i.e. no fatigue). Further, during activity rising there is an $O_2$ deficit because muscle start using energy without sufficient $O_2$ supply (anaerobic processes). These would be eventually recovered at the end of the activity possibly contributing to rising HR beyond rest.

Preferably, said correction unit is configured to correct the heart rate signal generated during a cardiovascular drift phase during a physical activity phase by substituting detected heart rate values by heart rate values detected during the preceding steady phase. This improves the accuracy of the energy expenditure estimation.

The correction unit may be configured to correct the heart rate signal generated during a recovery phase by reducing or eliminating detected heart rate values deviating by more than a predetermined amount or percentage from a recovery correction threshold. The recovery correction threshold may be predetermined, but may also be individualized for the particular person. For instance, in an embodiment the correction unit is configured to use as recovery correction threshold a predetermined heart rate value, or a heart rate value detected in a resting phase before a physical activity phase, or a heart rate value detected at the beginning of a physical activity phase. The recovery correction threshold may be increased by the component of HR due to reversing anaerobic processes such as that defined by HR deficit during the rising phase. In an embodiment, the HR drift correction may aim to remove from inactive periods following a HR drifting activity that amount of HR related to the determined HR drift and not the amount due to oxygen deficit recorded during HR rising.

In another embodiment the cardiovascular drift determination unit is configured to determine, during a recovery phase, a cardiovascular drift phase by comparing heart rate values detected during a recovery phase with a recovery duration threshold. The recovery duration threshold may be predetermined, but may also be individualized for the particular person. For instance, in an embodiment the cardiovascular drift determination unit is configured to use as recovery duration threshold a predetermined heart rate value, or a heart rate value detected in a resting phase before a physical activity phase, or a heart rate value detected at the beginning of a physical activity phase.

To further improve the accuracy of the energy expenditure estimation, the cardiovascular drift determination unit may further be configured to use a recovery duration threshold that is dependent on elapsed time from the end of a preceding activity period, and/or a percentage of a heart rate value detected in a resting phase, and/or the fitness level of the person, and/or the amount of cardiovascular drift determined during preceding activity phases, and/or the deficit in heart rate detected during a rising phase compared to a heart rate detected during a steady phase or at the end of a rising phase.

As mentioned above, in a physical activity period different phases may be distinguished. For this process the cardiovascular drift determination unit is preferably configured to determine a rising phase, a steady phase and/or a cardiovascular drift phase by use of the intensity of the physical activity, averages of heart rate determined during a time interval and respective thresholds.

Preferred embodiments of said movement sensor are an acceleration sensor or a gyroscope or GPS or any tool capable of sensing human purposeful body motion. Preferred embodiments of said heart rate sensor are a photoplethysmography sensor or an ECG sensor or a heart sound sensor capable of detecting heart beats.

The system further may further comprise one or more cardiovascular drift related signal acquisition units for acquiring one or more cardiovascular drift related signals carrying information on one or more of amount of sweat, weight loss, temperature rise, blood lactate concentration and physical fatigue of the person. Said cardiovascular drift related signal acquisition units may e.g. include a sweat sensor, a weight measurement unit, a temperature sensor, a measurement unit for measuring blood lactate concentration and/or a sensor for detecting fatigue of the person. Thus, the one or more cardiovascular drift related signal acquisition units may include one or more wearable sensors, remote sensors or connected devices.

Said movement sensor, said heart rate sensor and/or said device, preferably all those components, are built into a body worn device, in particular a wristband, wristwatch, smartphone or body belt. In other embodiments, only the sensors are worn on the patient's body, while the device, which is preferably implemented by a processor and/or by software (such as an app), may be arranged far from the patient, e.g. in a computer, laptop, tablet, smartphone, etc. In this case a connection is established between the sensors and the device, e.g. as wireless connection (such as using WLAN or Bluetooth or the like) or as wired connection. The device may also be implemented in a fitness device or exercise machine as used at home or in gyms.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
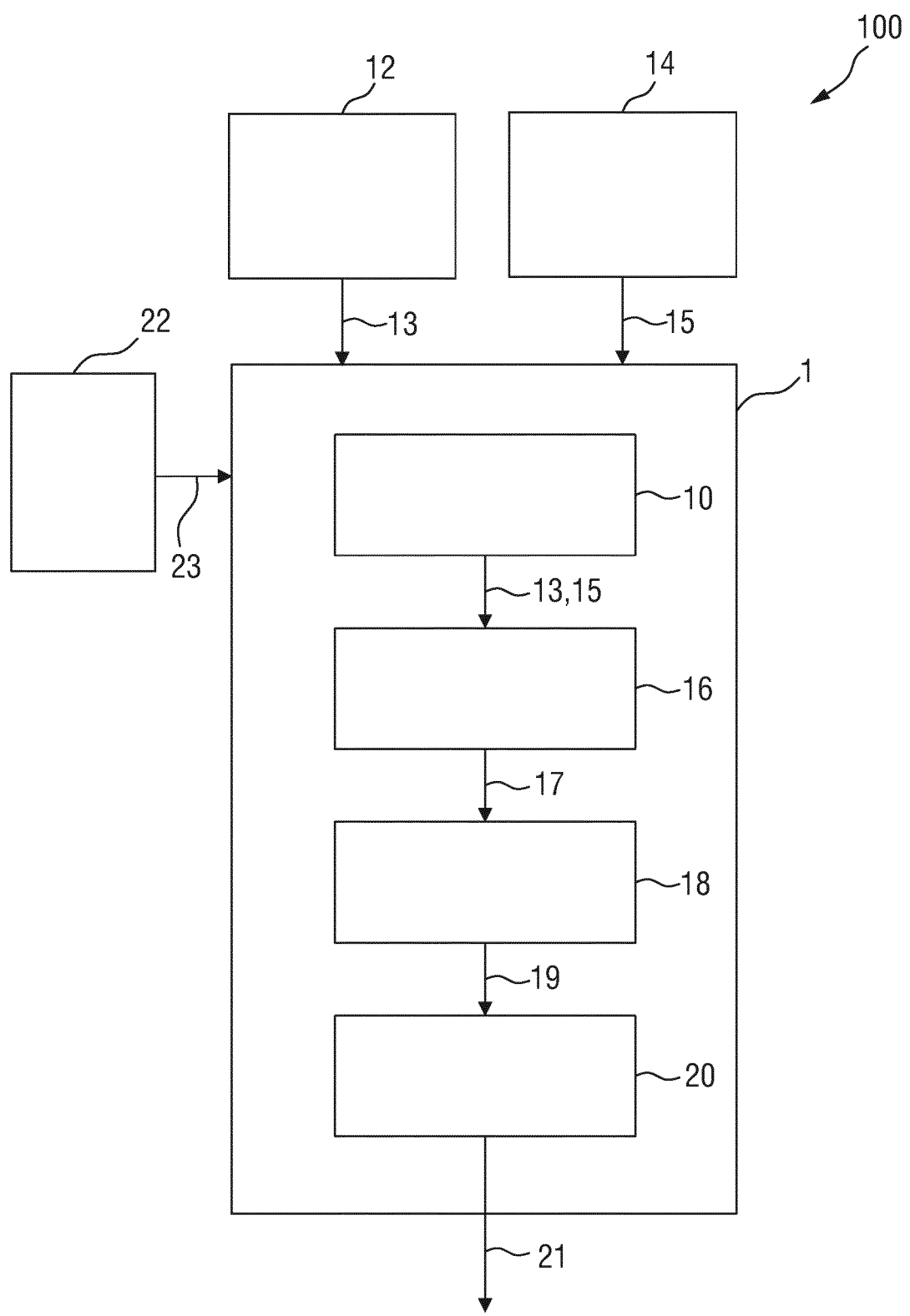
FIG. 1 shows a schematic diagram of an embodiment of a system and a device according to the present invention.

FIG. 1 shows a schematic diagram of an embodiment of a system 100 and a device 1 according to the present invention for estimating the energy expenditure of a person. The system 100 comprises a movement sensor 12 for detecting physical activity of the person and for generating a movement signal 13, a heart rate sensor 14 for detecting the heart rate of the person and for generating a heart rate signal 15, and a device 1 for estimating the energy expenditure of a person.

Optionally, the system 100 may further comprises one or more cardiovascular drift related signal acquisition units 22 for acquiring one or more cardiovascular drift related signals 23 carrying information on one or more of amount of sweat, weight loss, temperature rise, blood lactate concentration and physical fatigue of the person. Said cardiovascular drift related signal acquisition units 22 may e.g. include a sweat sensor, a weight measurement unit, a temperature sensor, a measurement unit for measuring blood lactate concentration and/or a sensor for detecting fatigue of the person.

Said movement sensor 12 may comprise an acceleration sensor or a gyroscope or GPS for determining intensity, modality and/or type of activity and said heart rate sensor 14 may comprise a photoplethysmography sensor or an ECG sensor or a heart sound sensor capable of detecting heart beats.

The device 1 comprises an input unit 10 for obtaining the movement signal 13 representing physical activity of the person and the heart rate signal 15 representing the heart rate of the person. The device 1 further comprises a cardiovascular drift determination unit 16 for determining cardiovascular drift phases 17 from said movement signal 13 and, in addition to the movement signal, either said heart rate signal 15 and/or one or more cardiovascular drift related signals 23 (preferably, if needed or used, also received by the input unit 10) carrying information on one or more of amount of sweat, weight loss, temperature rise, blood lactate concentration and physical fatigue of the person. The device 1 further comprises a correction unit 18 for correcting the heart rate signal 15 generated and representing the heart rate during a cardiovascular drift phase, and an estimation unit 20 for estimating the energy expenditure 21 of the person from the corrected heart rate signal 19. The device 1 may be implemented in software running on a processor, or in hardware, or in a combination of soft- and hardware.

Figure 2:
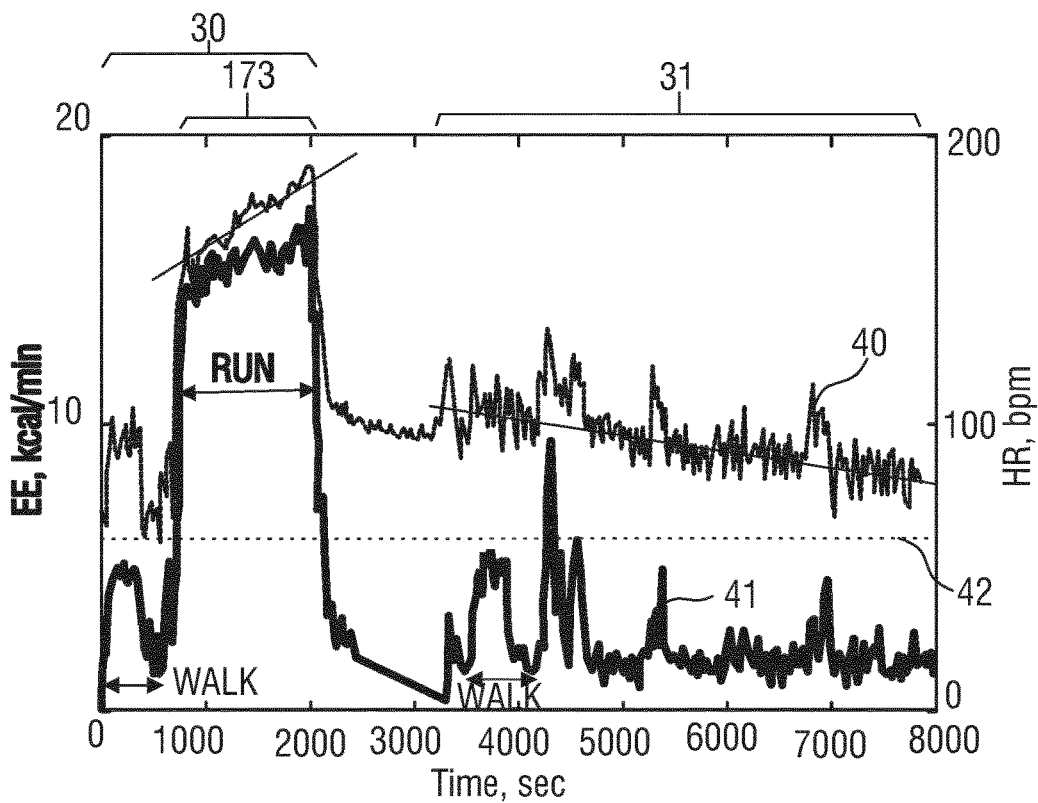
FIG. 2 shows a diagram illustrating cardiovascular drift occurring during running.

As explained above HR based estimates of energy expenditure are affected by cardiovascular drift. Cardiovascular drift causes overestimation errors of energy expenditure during physical activity in a physical activity phase 30 as well as during the recovery phase 31 following the physical activity phase 30 as illustrated in FIG. 2 showing a diagram illustrating cardiovascular drift 173 occurring during running. The increase in HR 40 during running is higher than what expected due to changes in energy expenditure (EE) 41. After running recovery of factors generating cardiovascular drift lasted for over 1.5 hours (5500 seconds) during which elevation of HR above resting value 42 is visible. These HR effects due to cardiovascular drift cause substantial overestimation errors of energy expenditure. In an embodiment the onset and likelihood of cardiovascular drift during physical activity is determined by analyzing HR dynamics in relation to changes in exercise intensity. The HR dynamics during physical activity may be modeled as a three-stage process composed by a rising phase, a steady phase and a drift phase. The rising phase corresponds to the beginning of an activity, during which HR rises quickly to reach a level sufficiently high to meet the initial energy demand. The steady phase corresponds to the period in which HR stops increasing or increases at a lower rate than the rising phase while exercise intensity is kept stable. This second phase may or may not be present due to exercise intensity and fitness level of the user. Indeed, for high exercise intensity and low fitness level the steady phase may be absent given an anticipation of the drift phase. The drift phase corresponds usually to the last period of an activity and manifests itself as an increase in HR beyond what is expected due to energy expenditure (exercise intensity, oxygen consumption).

Once the HR drift phase is detected or the probability of HR drifting is greater than a certain percentage the device 1, in particular the cardiovascular drift determination unit 16, determines the start time and the end time of the cardiovascular drift process. Alternatively, instead of determining start and end times of the cardiovascular drift process a contribution of HR drift may be added that is proportional to the likelihood of HR drift occurrence. The probability of HR drifting may be determined by concurrently looking at changes in HR and activity intensity within an exercise.

Activity intensity, activity modality and type may be determined by means of wearable sensors, mobile sensors or environmental sensors (i.e. generally one or more movement sensor(s) 12). For example, a wearable accelerometer can be used to determine activity type (e.g. walking, running, cycling) as well as exercise intensity (e.g. ambulatory speed, motion level). HR throughout the exercise can also be determined using wearable sensors.

In the following embodiments to determine the onset, termination and HR relative to the three phases that characterize HR dynamics during physical activity will be described.

The rising phase of an activity may be determined by analyzing HR dynamics and activity context over time. The cardiovascular drift determination unit 16 may be initialized when an activity module, e.g. a movement sensor, detects the start of an activity or exercise (walking, running, cycling, sport, etc.). Changes in HR over time (e.g. on a sec-by-sec basis) may be used to infer whether the rising phase has started and stopped. The largest change in HR from the beginning of the rising phase (dHRdtmax) may be determined iteratively after initialization to zero. At each time point (for example every second) the average HR is used to determine the change in HR (dHRdt) over two consecutive intervals. A buffer of data (dHRbuffer) accumulating dHRdt values for a certain period of time (e.g. 5 seconds) is updated iteratively. Such a buffer may be used as a moving average filter to the dHRdt values, and the smoothed dHRdt (smtdHR) may be calculated as the average of such data buffer at each time interval. If smtdHR is greater than a predetermined amount of beats per minute (e.g. 1 bpm) and the variable indicating the start of a rising period is false, the start of a rising phase (rising HR period) is set to the current interval. Afterwards if the dHRdtmax is lower than the current smtdHR, the maximum HR change during the rising phase is updated to the current smtdHR. When the smoothed HR change falls below a predetermined percentage (e.g. 25%) of dHRdtmax, the rising phase will be considered ended. In this way the start time (T_startrise), the end time (T_endrise), and the HR at the end of the rising phase (HR_endrise) during physical activity can be determined.

Figure 3:
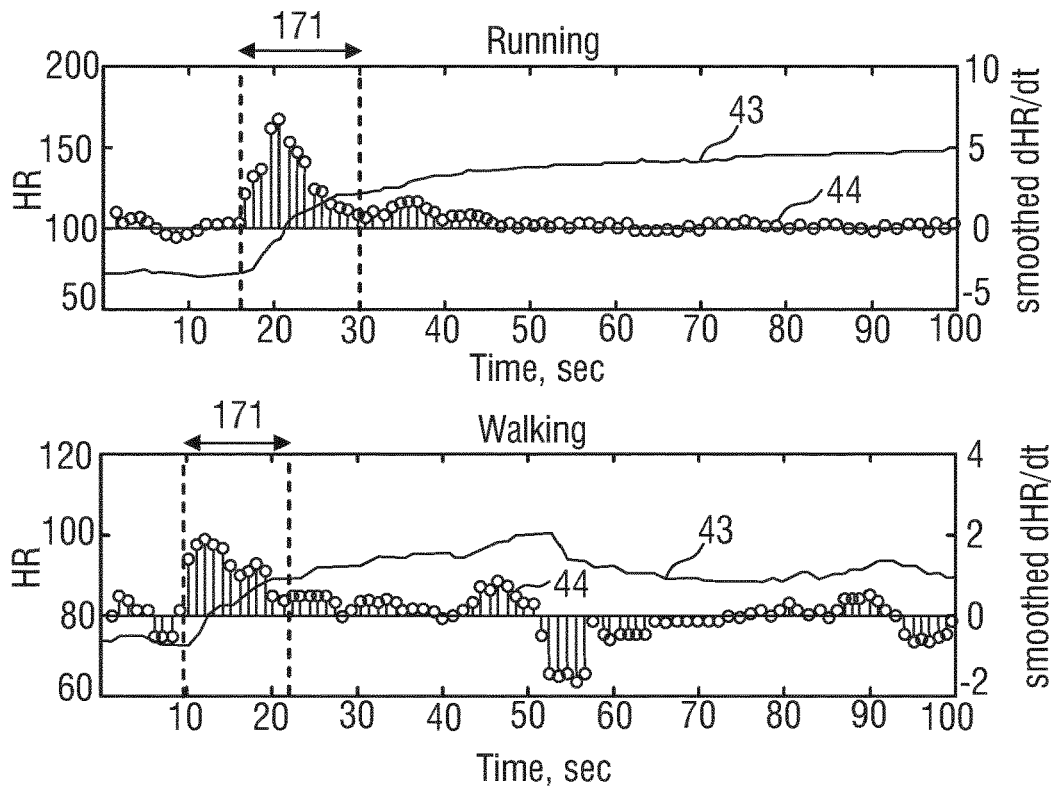
FIG. 3 shows a diagram illustrating the determination of a HR rising phase.

FIG. 3 shows a diagram illustrating the determination of a HR rising phase 171 from HR data 43 over time. Smoothed HR indicates the second-by-second change in HR averaged over 5 seconds. After activity onset, as determined by the activity module, the HR rising phase 171 is detected by analyzing the value of smoothed HR changes (smtdHR) 44. Once the smoothed dHR/dt 44 will return to values close to zero (e.g. a certain percentage of the maximum smoothed HR change value) the HR rising phase 171 will be considered over.

The steady phase (also called steady-state phase) of the activity will begin with the end of the rising phase and its duration may be determined by calculating a score or likelihood of cardiovascular drift. When the risk of cardiovascular drift is and stays low the presence of a steady-state period would be detected in which HR does not increase disproportionately with respect to activity intensity. This process begins from the end of the rising phase. The likelihood of cardiovascular drift may be calculated by concurrently looking at percentage changes in HR and activity intensity from the values registered at the end of the rising phase. Percentage changes in activity intensity can be expressed as variation in ambulatory speed, workload, or body movement as measured using e.g. a wearable accelerometer, etc.

In an implementation activity intensity is determined by activity level, which represents the variability in the wrist acceleration signal. A drift score may be determined by adjusting percentage changes in HR for the percentage change in intensity during physical activity. The drift score may then be used to determine the probability of cardiovascular drift by applying a logit function to the drift scores normalized to the 10% value. This is done to make sure that a 10% drift score corresponds to 50% probability of cardiovascular drift and that a 40% drift score corresponds to 95% probability of cardiovascular drift. Different percentage normalization thresholds for drift score can also be chosen or personalized according to the fitness level of the user. For users with good to superior fitness level the drift score can be normalized to ensure 50% drift probability at 5% drift score. If the drift probability is above a certain threshold (e.g. 75%) the end of the steady state phase is set.

Figure 4:
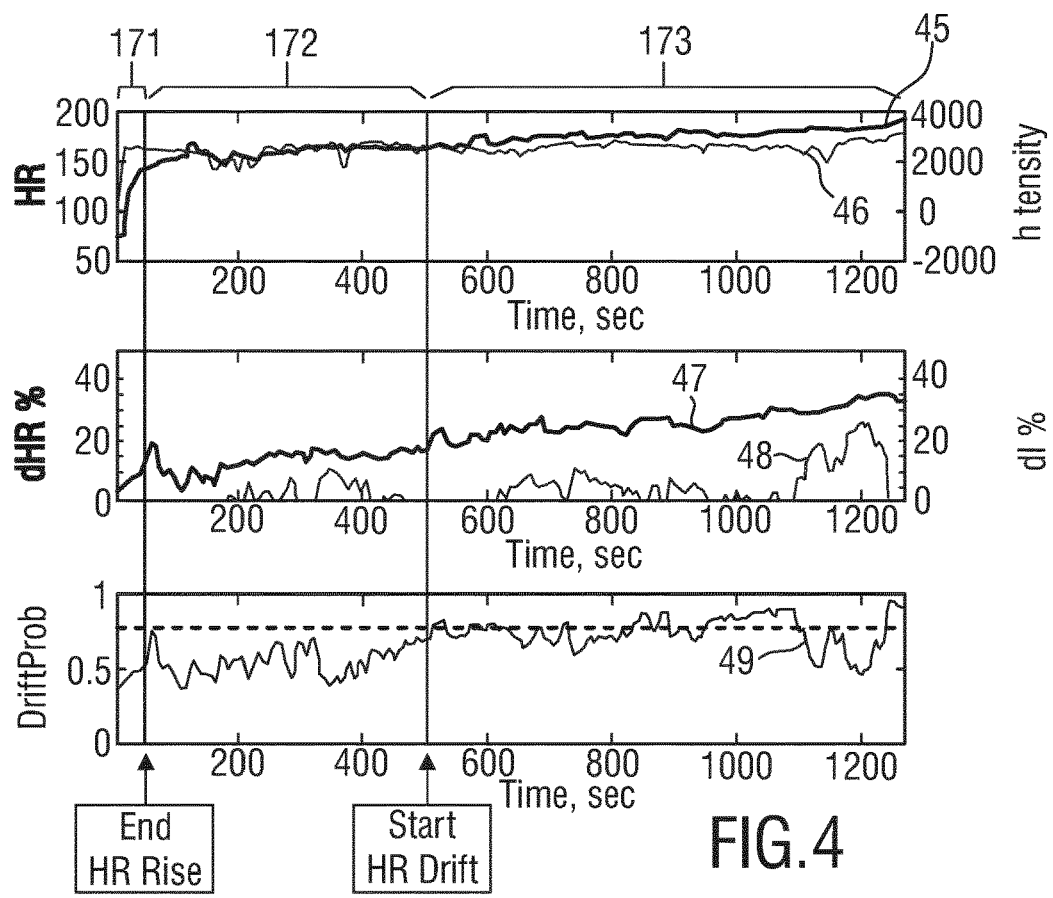
FIG. 4 shows a diagram illustrating the determination of cardiovascular drift and a HR steady state phase.

FIG. 4 shows a diagram illustrating the determination of cardiovascular drift phase 173 and a HR steady state phase 172. The plot on top shows the HR 45 and activity intensity (activity counts) 46 measured during a free-living running exercise. This plot shows that HR 45 tends to increase over time while activity intensity 46 seems to randomly fluctuate around the mean. The plot in the middle shows the percentage change 47 in HR and the percentage change 48 in activity intensity as compared to the HR and intensity values measured at the end of the rising phase 171. The plot on the bottom shows the cardiovascular drift probability 49 as determined by the presented method. Start of HR drift phase 173 and termination of the steady state phase 172 is determined by the time point when the drift probability exceeds a predetermined threshold, e.g. a threshold of 75% in this example.

The drift phase is defined by the end of the steady phase and would last until the end of the exercise unless the exercise intensity and the HR change will make the drift probability to drop below a predetermined threshold (e.g. 25%).

Figure 5A:
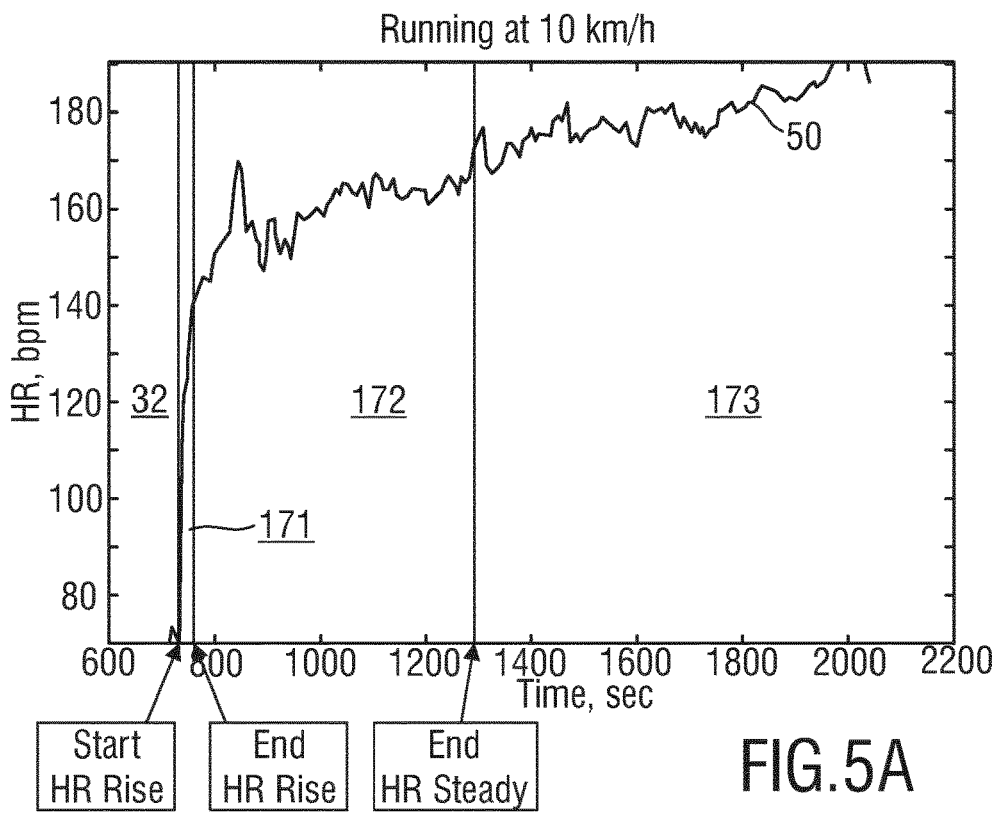
FIG. 5 shows diagrams illustrating the determination of a HR rising phase, a HR steady phase, and a drift phase during running and walking, respectively.
Figure 5B:
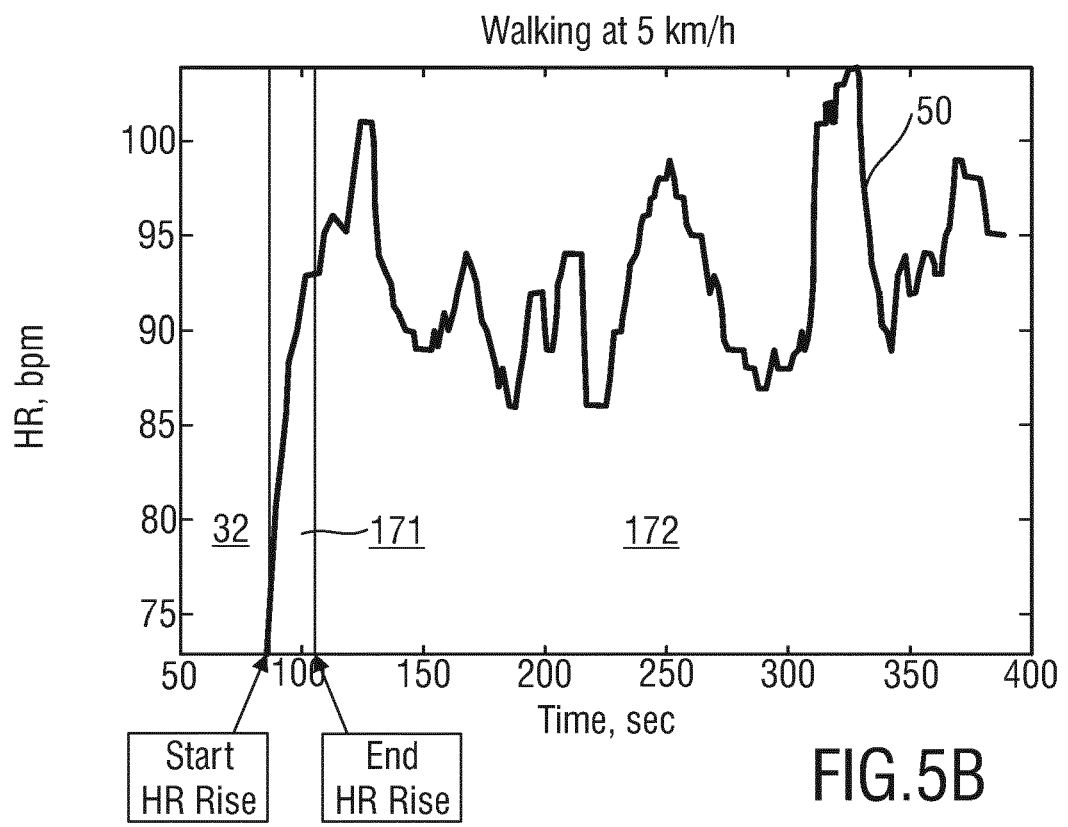

FIG. 5 shows diagrams illustrating the determination of a HR rising phase 171, a HR steady phase 172, and a drift phase 173 during running at 10 km/h (FIG. 5A) and walking at 5 km/h (FIG. 5B), respectively. Cardiovascular drift was correctly not detected during this activity in the execution period.

Cardiovascular drift can be caused by physiological factors triggered during physical activity such as de-hydration, vasodilatation, heat, catecholamine accumulation and muscle fatigue. However, even when the physical activity, that causes the drift, ends, the drift does not immediately disappear. This means that even after physical activity, HR may remain substantially elevated above the resting level causing overestimation errors of energy expenditure as illustrated in FIG. 2. An embodiment of proposed device and method is configured to deal with the problem of identifying those periods during which HR is elevated during activity recovery in an activity recovery phase 31.

Once an activity has been detected and e.g. a HR trend analysis suggested that a HR drift period occurred, HR data is processed during activity recovery to determine correction factors for HR prior to calculation of energy expenditure. These correction factors can be designed using different models and the parameters of such models can be personalized according to previous measurements or according to user's characteristics of fitness level. An embodiment of proposed device and method is configured to use contextual data, temporal information and the magnitude of the cardiovascular drift experienced during physical activity to adjust HR measurements prior to energy expenditure prediction to avoid overestimation errors in the recovery period 31 following a physical activity period 30.

This embodiment is based on calculating whether after an activity the HR returns to levels sufficiently close to that registered in resting conditions. More specifically, in periods of inactivity (after exercise) the HR 50 is compared to the resting HR or the HR measured in resting periods 32 (see FIG. 5) before the exercise. Only when the HR 50 reaches levels below a certain threshold, the HR recovery phase will be considered terminated and no further correction to HR is applied. The threshold can be designed in different ways, it can be made dependent on elapsed time from the end of an activity, dependent on a percentage of the resting HR, according to the fitness level of the user, or according to the amount of cardiovascular drift registered during the previous activities, or according to the deficit in HR recorded during HR rising as compared to HR e.g. in steady state or at the end of a rising phase.

The HR deficit during activity rising (HRriseDeficit) may be determined and then used together with resting HR (determined before exercise) as threshold (BasalHR) to judge whether the recovery phase from drifting factors has terminated. The HRriseDeficit component of BasalHR may be reduced over time according to an exponential function. Then, the start and the end time of the recovery phase may be determined together with a HR correction value (HRrest_correction). HRrest_correction may be calculated recursively over time during the recovery phase as the difference between a smoothed HR from inactive periods (baselineHR) and the BasalHR value. This new variable (HRrest_correction) may be used to correct HR values between the start and end of the recovery phase to eliminate from HR contributions due to recovery from cardiovascular drift. The end recovery phase may be determined when the HRrest correction gets close to zero or when HR reaches levels close to BasalHR.

Figure 6:
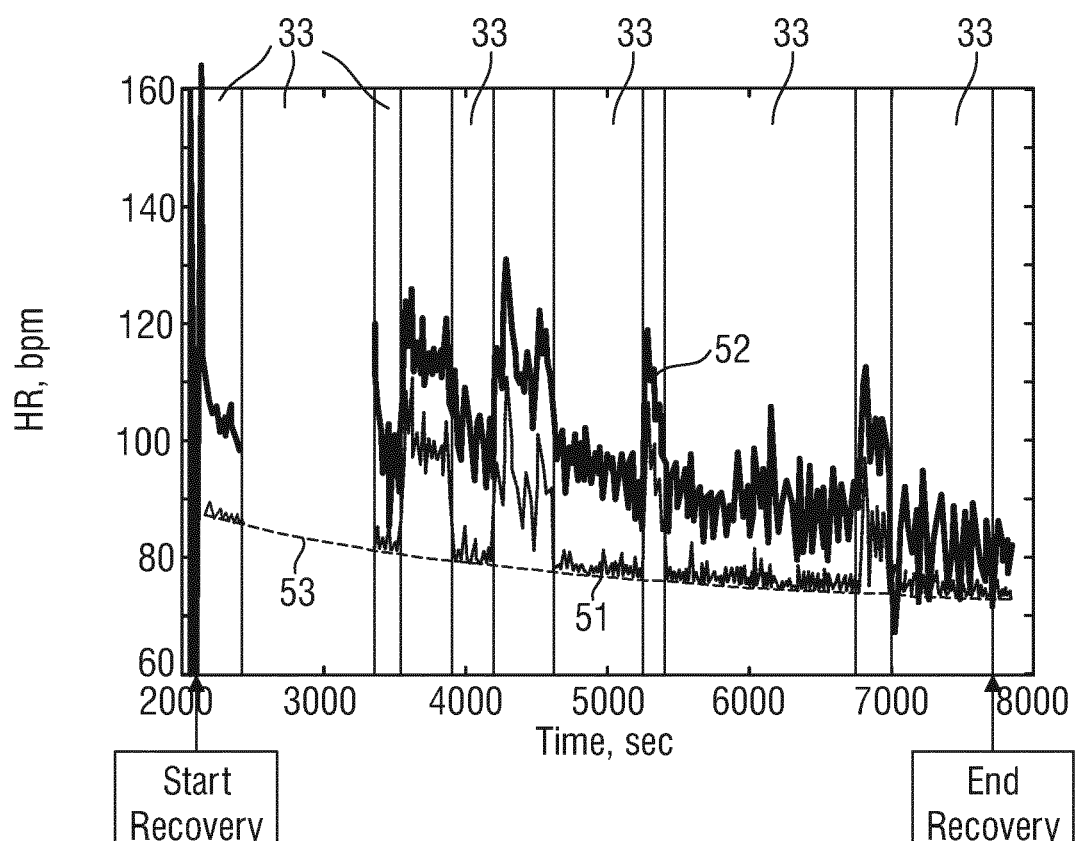
FIG. 6 shows a diagram illustrating the HR correction during a recovery phase.

BasalHR indicates an elevation of HR above resting, which is metabolically relevant, and can explain some of the additional need in oxygen and energy expenditure to recover from metabolic deficit processes occurring during physical activity. The difference between the BasalHR and the smoothed HR recorded in inactive periods during recovery is the amount of HR unrelated to energy expenditure which causes severe overestimation of energy expenditure in this phase following cardiovascular drift and exercise. An example of the output of this processing is depicted in FIG. 6 showing a diagram illustrating the HR correction during a recovery phase for determining the HR correction during recovery from cardiovascular drift and exercise. FIG. 6 particularly shows the corrected HR 52 resulting from the subtraction between HR 51 and a correction factor. The correction factor changes over time and results from the difference between a smoothed HR during inactive periods 33 and a basal HR 53 which is the sum between resting HR and the HR deficit calculated during activity rising.

Figure 7:
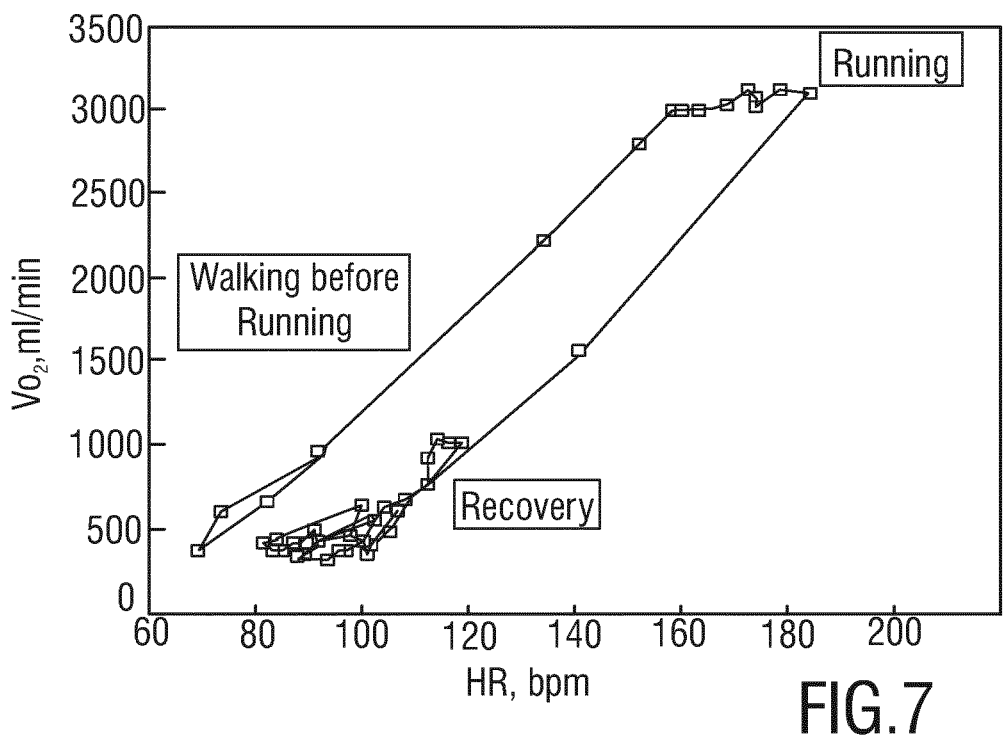
FIG. 7 shows a diagram illustrating the hysteresis phenomenon observed in the relationship between HR and VO2 as influenced by cardiovascular drift during a physical activity phase and during a recovery phase.

Once periods of cardiovascular drift have been identified during physical activity and recovery following exercise, HR data is corrected to avoid overestimation errors in energy expenditure prediction models. The correction applied to HR data is made to maintain a valid unique and linear relationship between HR and oxygen consumption (VO2) or energy expenditure. Cardiovascular drift causes hysteresis type of distortion to the relationship between HR and VO2 and energy expenditure as depicted in FIG. 7 showing a diagram illustrating the hysteresis phenomenon observed in the relationship between HR and VO2 as influenced by cardiovascular drift during a physical activity phase (in this example running) and during a subsequent recovery phase.

Figure 8:
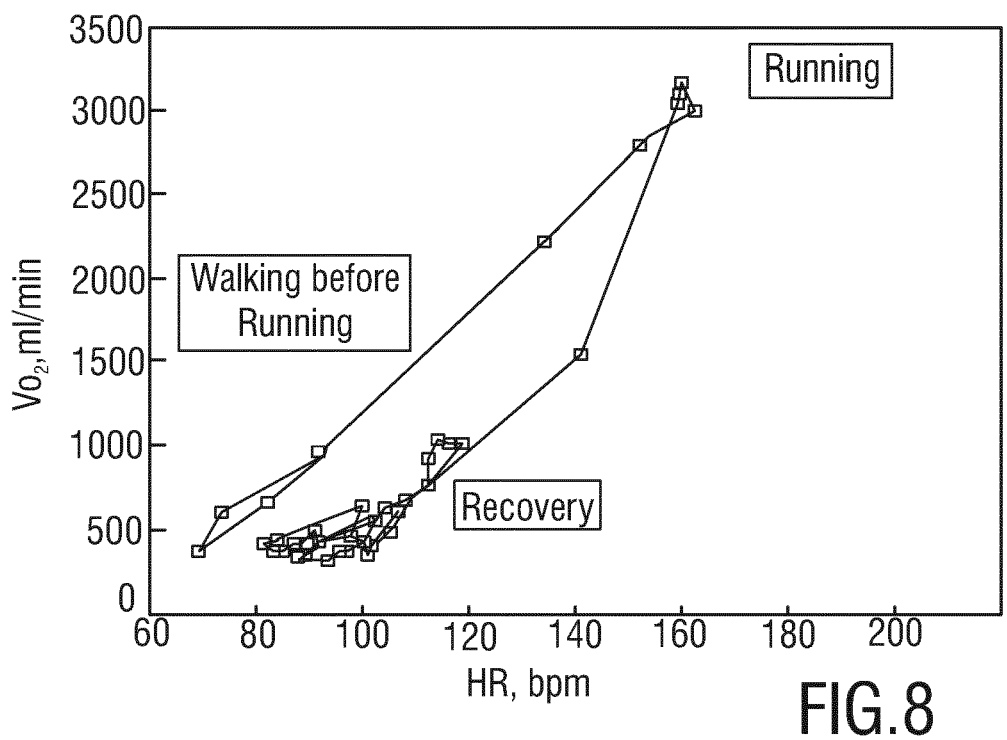
FIG. 8 shows a diagram illustrating the HR correction during a physical activity phase.

A solution to this problem may be to substitute HR values recorded during the cardiovascular drift phase of an activity with the HR values recorded during the steady state phase as illustrated in FIG. 8 showing a diagram illustrating the HR correction during a physical activity phase. Correction of cardiovascular drift during running improves the problem of cardiovascular drift increasing accuracy for energy expenditure estimated during running.

Figure 9:
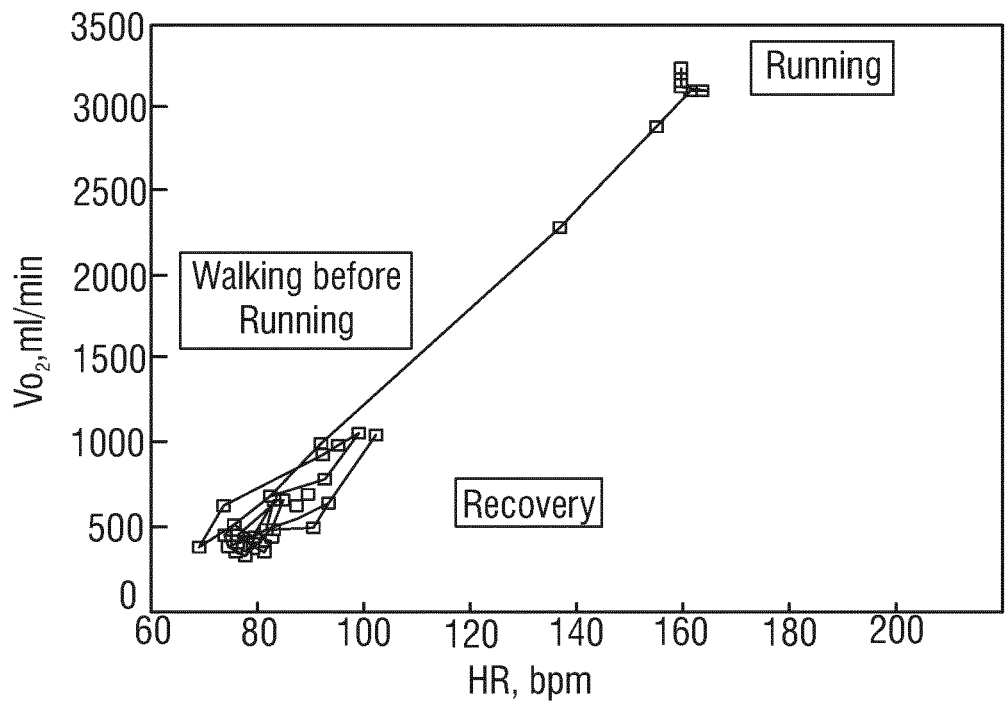
FIG. 9 shows a diagram illustrating the HR correction during a recovery phase.

In a further improvement any elevation in HR in the recovery periods following a drifting activity may be removed by an amount unexplained by resting HR nor HR deficit during HR rising as illustrated in FIG. 9 showing a diagram illustrating the HR correction during a recovery phase. Correction of cardiovascular drift during running and recovery substantially increases accuracy for energy expenditure estimated during the entire monitoring period and eliminates the hysteresis problem in the relationship between HR and VO2.

By applying both corrections illustrated in FIGS. 8 and 9 to HR measurements an elimination of the hysteresis problem in the relationship between HR and VO2 during drifting activity and recovery is clearly visible.

Once drift phases have been identified during physical activity and the activity recovery period has been analyzed, HR values are appropriately and adaptively corrected over time to represent a valid input to the estimation of energy expenditure. The energy expenditure may thus be a function of this kind:

$$EE(t)=f(CorrectedHR, activity\ type, BMR, subject\ characteristics, fitness\ level).$$

Figure 10:
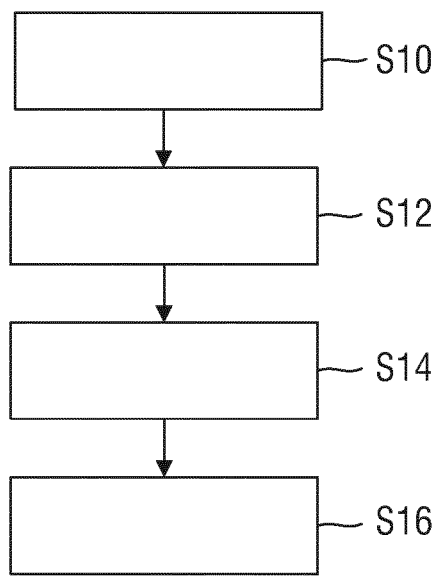
FIG. 10 shows a flow chart illustrating an embodiment of a method according to the present invention.

FIG. 10 shows a flow chart illustrating an embodiment of a method according to the present invention. In a first step S10 a movement signal representing physical activity of the person and a heart rate signal representing the heart rate of the person are obtained. In a second step S12 cardiovascular drift phases are determined from said movement signal and either said heart rate signal and/or one or more cardiovascular drift related signals. In a third step S14 the heart rate signal generated and representing the heart rate during a cardiovascular drift phase is corrected. In a fourth step S16 the energy expenditure of the person is estimated from the corrected heart rate signal.

Figure 11:
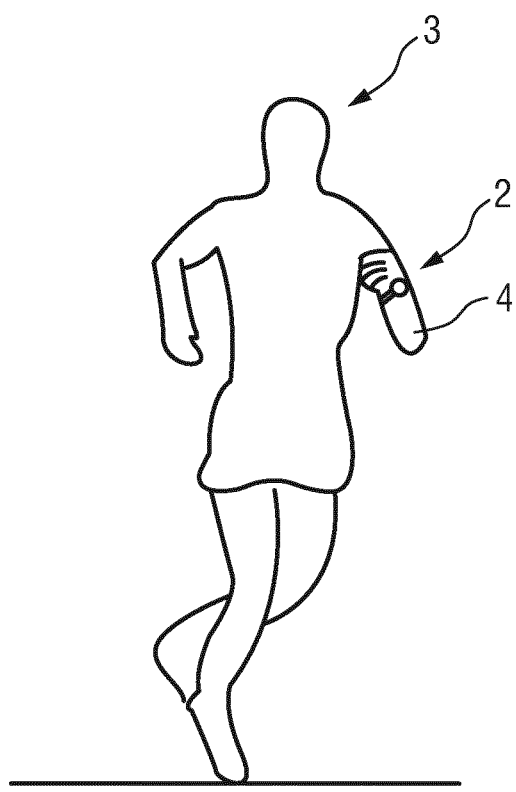
FIG. 11 shows an exemplary embodiment of the system according to the present invention.

Generally, any HR sensor (sometimes also referred to as HR monitor) can be used in combination with a movement sensor (sometimes also referred to as activity monitor). An example of an integrated device which can be used for this purpose is an optical HR sensor containing a photo-plethysmography sensor (for HR detection) and a 3-axial accelerometer (for activity detection) as e.g. described in WO 2013/038296 A1. Such an integrated device, preferably including all components of the system 100 shown in FIG. 1, may be implemented as a wrist worn device 2 as exemplarily shown in FIG. 11, which can be worn by a user 3 at his arm 4. This technology allows monitoring HR unobtrusively and comfortably at any location on the body (for example at the wrist). This embodiment is ideal since users will have their fitness evaluation done just by wearing a watch or bracelet throughout the day and possibly night.

Generally, other kinds of HR sensors and movement sensors can be used in a device and method according to the present invention as well. For instance, as HR sensor an ECG sensor may be used, and as movement sensor one or more motion sensors may be used. Other examples of HR sensors are PPG sensors, and camera PPG sensors and GPS can be also used as movement sensor.

Activity monitoring solutions in the personal health space are oriented towards providing accurate information to the user regarding activity level and energy expenditure with respect to daily targets. Innovative personal health monitoring services highly rely on the accuracy of the wearable activity monitor to generate user satisfaction during the activity intervention. The device is often used as a carrier of information on the daily achievements. Poor accuracy of the method to assess activity intensity and calories expenditure leads to user dissatisfaction and causes a dramatic decrease in the net promoter score (NPS) for the solution. New activity monitors, which may use or include the device or method according to the present invention have the potential to provide highly accurate energy expenditure estimates given the ability to record heart rate data together with body movement, in particular body acceleration.

Applications of the device system and method of the present invention include algorithms and computational methods used in wearable HR and activity monitors aimed at accurately estimating energy expenditure and interpreting user physiological parameters to assess stress, cardio-respiratory fitness, exercise recovery etc. Products could use this invention to provide users and customers with more accurate estimates of energy expenditure.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for estimating the energy expenditure of a person comprising:
    an input unit for obtaining, from a movement sensor, a movement signal representing physical activity of the person and obtaining, from a heart rate sensor, a heart rate signal representing a heart rate of the person,
    a cardiovascular drift determination unit for determining a cardiovascular drift phase from said movement signal and at least one of said heart rate signal or one or more cardiovascular drift related signals carrying information on one or more of an amount of sweat, a weight loss, a temperature rise, a blood lactate concentration or a physical fatigue of the person,
    a correction unit for correcting the heart rate signal representing the heart rate of the person during the cardiovascular drift phase, and
    an estimation unit for estimating the energy expenditure of the person from the corrected heart rate signal.

2. The device as claimed in claim 1,
    wherein said cardiovascular drift determination unit is configured to determine one or more of an onset, a duration, an end or a likelihood of the cardiovascular drift phase.

3. The device as claimed in claim 1,
    wherein said cardiovascular drift determination unit is configured to determine a first cardiovascular drift phase during a physical activity phase and a second cardiovascular drift phase during a recovery phase succeeding the physical activity phase.

4. The device as claimed in claim 3,
    wherein said cardiovascular drift determination unit is further configured to determine, during the physical activity phase, a rising phase and a steady phase.

5. The device as claimed in claim 4,
    wherein said correction unit is configured to correct the heart rate signal generated during the first cardiovascular drift phase during the physical activity phase by substituting detected heart rate values with heart rate values detected during the preceding steady phase.

6. The device as claimed in claim 4, wherein said cardiovascular drift determination unit is configured to determine one or more of the rising phase, the steady phase or the first cardiovascular drift phase by use of an intensity of the physical activity, averages of heart rate determined during a time interval and respective thresholds.

7. The device as claimed in claim 3, wherein said correction unit is configured to correct the heart rate signal generated during the recovery phase by reducing or eliminating detected heart rate values deviating by more than a predetermined amount or percentage from a recovery correction threshold.

8. The device as claimed in claim 7, wherein said correction unit is configured to use as the recovery correction threshold a predetermined heart rate value, or a heart rate value detected in a resting phase before the physical activity phase, or a heart rate value detected at the beginning of the physical activity phase.

9. The device as claimed in claim 3, wherein said cardiovascular drift determination unit is configured to determine, during the recovery phase, the second cardiovascular drift phase by comparing heart rate values detected during the recovery phase with a recovery duration threshold.

10. The device as claimed in claim 9, wherein said cardiovascular drift determination unit is configured to use as the recovery duration threshold a predetermined heart rate value, or a heart rate value detected in a resting phase before the physical activity phase, or a heart rate value detected at the beginning of the physical activity phase.

11. The device as claimed in claim 9, wherein said cardiovascular drift determination unit is configured to use as the recovery duration threshold a value that is dependent on one or more of an elapsed time from the end of a preceding activity period, or a percentage of a heart rate value detected in a resting phase, or a fitness level of the person, or an amount of cardiovascular drift determined during preceding activity phases, or a deficit in heart rate detected during a rising phase compared to a heart rated detected during a steady phase or at the end of a rising phase.

12. A system for estimating the energy expenditure of a person, comprising:
a movement sensor for detecting physical activity of the person and for generating a movement signal,
a heart rate sensor for detecting the heart rate of the person and for generating a heart rate signal, and
a device for estimating the energy expenditure of a person as claimed in claim 1.

13. The system as claimed in claim 12, wherein said movement sensor comprises one or more of an acceleration sensor, a gyroscope, or a GPS for determining one or more of intensity, modality or type of activity,
wherein said heart rate sensor comprises one or more of a photoplethysmography sensor, an ECG sensor, or a heart sound sensor capable of detecting heart beats, and
wherein said system further comprises one or more cardiovascular drift related signal acquisition units for acquiring one or more cardiovascular drift related signals carrying information on one or more of amount of sweat, weight loss, temperature rise, blood lactate concentration or physical fatigue of the person.

14. A computer-implemented method for estimating the energy expenditure of a person, comprising:
obtaining by the computer an electronic movement signal from a movement sensor, the movement signal representing physical activity of the person, and an electronic heart rate signal from a heart rate sensor, the heart rate signal representing the heart rate of the person,
determining by the computer a cardiovascular drift phase from said movement signal and at least one of said heart rate signal or one or more cardiovascular drift related signals carrying information on one or more of an amount of sweat, a weight loss, a temperature rise, a blood lactate concentration or a physical fatigue of the person,
correcting by the computer the heart rate signal generated and representing the heart rate during the cardiovascular drift phase, and
estimating by the computer the energy expenditure of the person from the corrected heart rate signal.

15. The method of claim 14, further comprising determining one or more of an onset, a duration, an end or a likelihood of the cardiovascular drift phase.

16. The method of claim 14, wherein a first cardiovascular drift phase is determined during a physical activity phase and a second cardiovascular drift phase is determined during a recovery phase succeeding the physical activity phase.

17. The method of claim 16, wherein a rising phase and a steady phase are determined during the physical activity phase.

18. The method of claim 17, wherein one or more of the rising phase, the steady phase or the first cardiovascular drift phase are determined by use of an intensity of the physical activity, averages of heart rate determined during a time interval and respective thresholds.

19. The method of claim 16, further comprising correcting the heart rate signal generated during the recovery phase by reducing or eliminating detected heart rate values deviating by more than a predetermined amount or percentage from a recovery correction threshold.

20. The method of claim 19, wherein the recovery correction threshold includes a predetermined heart rate value, or a heart rate value detected in a resting phase before the physical activity phase, or a heart rate value detected at the beginning of the physical activity phase.

21. The method of claim 16, wherein determining the second cardiovascular drift phase during the recovery phase comprises comparing heart rate values detected during the recovery phase with a recovery duration threshold.

22. The method of claim 21, wherein the recovery duration threshold includes a predetermined heart rate value, or a heart rate value detected in a resting phase before the physical activity phase, or a heart rate value detected at the beginning of the physical activity phase.

23. The method of claim 21, wherein the recovery duration threshold is a value that is dependent on one or more of an elapsed time from the end of a preceding activity period, or a percentage of a heart rate value detected in a resting phase, or a fitness level of the person, or an amount of cardiovascular drift determined during preceding activity phases, or a deficit in heart rate detected during a rising phase compared to a heart rated detected during a steady phase or at the end of a rising phase.

24. The method of claim 14, wherein correcting the heart rate signal generated during the cardiovascular drift phase comprises correcting the heart rate signal during a physical activity phase by substituting detected heart rate values with heart rate values detected during a preceding steady phase.

25. The method of claim 14, wherein the movement sensor comprises one or more of an acceleration sensor, a gyroscope, or a GPS for determining one or more of intensity, modality or type of activity, and wherein the heart rate sensor comprises one or more of a photoplethysmography sensor, an ECG sensor, or a heart sound sensor capable of detecting heart beats.

26. At least one non-transitory computer readable storage medium comprising computer program code which, when executed by a computing system, causes the computing system to:
  obtain an electronic movement signal from a movement sensor, the movement signal representing physical activity of a person, and an electronic heart rate signal from a heart rate sensor, the heart rate signal representing the heart rate of the person;
  determine a cardiovascular drift phase from said movement signal and at least one of said heart rate signal or one or more cardiovascular drift related signals carrying information on one or more of an amount of sweat, a weight loss, a temperature rise, a blood lactate concentration or a physical fatigue of the person;
  correct the heart rate signal generated and representing the heart rate during the cardiovascular drift phase; and
  estimate the energy expenditure of the person from the corrected heart rate signal.

27. The at least one non-transitory computer readable storage medium of claim 26, wherein the computer program code, when executed, further causes the computing system to determine one or more of an onset, a duration, an end or a likelihood of the cardiovascular drift phase.

28. The at least one non-transitory computer readable storage medium of claim 26, wherein a first cardiovascular drift phase is determined during a physical activity phase and a second cardiovascular drift phase is determined during a recovery phase succeeding the physical activity phase.

29. The at least one non-transitory computer readable storage medium of 28, wherein a rising phase and a steady phase are determined during the physical activity phase.

30. The at least one non-transitory computer readable storage medium of claim 29, wherein one or more of the rising phase, the steady phase or the first cardiovascular drift phase are determined by use of an intensity of the physical activity, averages of heart rate determined during a time interval and respective thresholds.

31. The at least one non-transitory computer readable storage medium of claim 28, wherein the computer program code, when executed, further causes the computing system to correct the heart rate signal generated during the recovery phase by reducing or eliminating detected heart rate values deviating by more than a predetermined amount or percentage from a recovery correction threshold.

32. The at least one non-transitory computer readable storage medium of claim 31, wherein the recovery correction threshold includes a predetermined heart rate value, or a heart rate value detected in a resting phase before the physical activity phase, or a heart rate value detected at the beginning of the physical activity phase.

33. The at least one non-transitory computer readable storage medium of claim 28, wherein to determine the second cardiovascular drift phase during the recovery phase comprises comparing heart rate values detected during the recovery phase with a recovery duration threshold.

34. The at least one non-transitory computer readable storage medium of claim 33, wherein the recovery duration threshold includes a predetermined heart rate value, or a heart rate value detected in a resting phase before the physical activity phase, or a heart rate value detected at the beginning of the physical activity phase.

35. The at least one non-transitory computer readable storage medium of claim 33, wherein the recovery duration threshold is a value that is dependent on one or more of an elapsed time from the end of a preceding activity period, or a percentage of a heart rate value detected in a resting phase, or a fitness level of the person, or an amount of cardiovascular drift determined during preceding activity phases, or a deficit in heart rate detected during a rising phase compared to a heart rated detected during a steady phase or at the end of a rising phase.

36. The at least one non-transitory computer readable storage medium of claim 26, wherein to correct the heart rate signal generated during the cardiovascular drift phase comprises to correct the heart rate signal during a physical activity phase by substituting detected heart rate values with heart rate values detected during a preceding steady phase.

37. The at least one non-transitory computer readable storage medium of claim 26, wherein the movement sensor comprises one or more of an acceleration sensor, a gyroscope, or a GPS for determining one or more of intensity, modality or type of activity, and wherein the heart rate sensor comprises one or more of a photoplethysmography sensor, an ECG sensor, or a heart sound sensor capable of detecting heart beats.

38. A device for estimating the energy expenditure of a person comprising:
  a computer readable storage medium comprising a set of instructions; and
  a processor configured to execute the set of instructions, wherein when executed the instructions cause the processor to perform operations comprising,
    obtaining, from a movement sensor, an electronic movement signal representing physical activity of the person,
    obtaining, from a heart rate sensor, an electronic heart rate signal representing the heart rate of the person,
    determining a cardiovascular drift phase from said movement signal and at least one of said heart rate signal or one or more cardiovascular drift related signals carrying information on one or more of an amount of sweat, a weight loss, a temperature rise, a blood lactate concentration or a physical fatigue of the person,
    correcting the heart rate signal representing the heart rate of the person during the cardiovascular drift phase, and
    estimating the energy expenditure of the person from the corrected heart rate signal.

39. The device of claim 38, wherein the instructions, when executed, further cause the processor to perform operations comprising determining one or more of an onset, a duration, an end or a likelihood of the cardiovascular drift phase.

40. The device of claim 38, wherein a first cardiovascular drift phase is determined during a physical activity phase and a second cardiovascular drift phase is determined during a recovery phase succeeding the physical activity phase.

41. The device of claim 40, wherein a rising phase and a steady phase are determined during the physical activity phase.

42. The device of claim 38, wherein correcting the heart rate signal generated during the cardiovascular drift phase comprises correcting the heart rate signal during a physical activity phase by substituting detected heart rate values with heart rate values detected during a preceding steady phase.

43. The device of claim 40, wherein the instructions, when executed, further cause the processor to perform operations comprising correcting the heart rate signal generated during the recovery phase by reducing or eliminating detected heart rate values deviating by more than a predetermined amount or percentage from a recovery correction threshold.

44. The device of claim 43, wherein the recovery correction threshold includes a predetermined heart rate value, or a heart rate value detected in a resting phase before the physical activity phase, or a heart rate value detected at the beginning of the physical activity phase.

45. The device of claim 40, wherein determining the second cardiovascular drift phase during the recovery phase comprises comparing heart rate values detected during the recovery phase with a recovery duration threshold.

46. The device of claim 45, wherein the recovery duration threshold includes a predetermined heart rate value, or a heart rate value detected in a resting phase before the physical activity phase, or a heart rate value detected at the beginning of the physical activity phase.

47. The device of claim 45, wherein the recovery duration threshold is a value that is dependent on one or more of an elapsed time from the end of a preceding activity period, or a percentage of a heart rate value detected in a resting phase, or a fitness level of the person, or an amount of cardiovascular drift determined during preceding activity phases, or a deficit in heart rate detected during a rising phase compared to a heart rated detected during a steady phase or at the end of a rising phase.

48. The device of claim 41, wherein one or more of the rising phase, the steady phase or the first cardiovascular drift phase are determined by use of an intensity of the physical activity, averages of heart rate determined during a time interval and respective thresholds.

49. The device of claim 38, wherein the movement sensor and the heart rate sensor are each integrated within said device.

50. The device of claim 49, wherein the movement sensor comprises one or more of an acceleration sensor, a gyroscope, or a GPS for determining one or more of intensity, modality or type of activity, and wherein the heart rate sensor comprises one or more of a photoplethysmography sensor, an ECG sensor, or a heart sound sensor capable of detecting heart beats.

* * * * *